United States Patent
Chhabada et al.

(10) Patent No.: US 6,906,062 B2
(45) Date of Patent: Jun. 14, 2005

(54) CRYSTALLINE FORM I OF 2-METHYL-4-(4-MENTHYL-1-PIPERAZINYL) 10H THIENO [2,3-B][1,5]BENZODIAZEPINE

(75) Inventors: Vijay Chhangamal Chhabada, Baroda (IN); Rajeev Budhdev Rehani, Baroda (IN); Rajamamannar Thennati, Baroda (IN)

(73) Assignee: Sun Pharmaceutical Industries Limited, Maharashtra (IN)

( * ) Notice: Subject to any disclaimer, the term of this patent is extended or adjusted under 35 U.S.C. 154(b) by 0 days.

(21) Appl. No.: 10/326,397

(22) Filed: Dec. 23, 2002

(65) Prior Publication Data

US 2003/0125322 A1 Jul. 3, 2003

(30) Foreign Application Priority Data

Dec. 24, 2001 (IN) .......................................... 1211/2001

(51) Int. Cl.[7] .......................... A61P 25/18; A61K 31/55; C07D 495/04
(52) U.S. Cl. ........................................ 514/220; 540/557
(58) Field of Search ............................ 514/220; 540/557

(56) References Cited

U.S. PATENT DOCUMENTS

| | | | |
|---|---|---|---|
| 5,229,382 A | 7/1993 | Chakrabarti et al. | 514/220 |
| 5,637,584 A * | 6/1997 | Larsen | 514/220 |
| 5,703,232 A | 12/1997 | Bunnell et al. | 540/557 |
| 5,736,541 A | 4/1998 | Bunnell et al. | 514/220 |

FOREIGN PATENT DOCUMENTS

| | | |
|---|---|---|
| WO | WO 98/12199 | 3/1998 |
| WO | WO 99 16312 | 4/1999 |
| WO | WO 01 47933 | 7/2001 |

* cited by examiner

*Primary Examiner*—Brenda Coleman
(74) *Attorney, Agent, or Firm*—Westerman, Hattori Daniels & Adrian LLP

(57) ABSTRACT

Crystalline Form I of 2-methyl-4-(4-methyl-1-piperazinyl)-10H-thieno[2,3-b][1,5]benzodiazepine characterised by x-ray powder diffraction peaks at approximately 9.94, 8.53, 8.19, 6.86, 6.35, 5.47, 4.83, 4.71, 4.53, 4.22, 4.08, 3.82, 3.75, 3.69, 3.50, 3.34, 3.11, 2.94, 2.82, 2.76, 2.59, 2.34, 2.03, 1.92 d (interplanar spacing) values; infrared absorbance bands at approximately 1456, 1365, 905, 757, 662 & 604 cm$^{-3}$ and having stable colour at ambient conditions of storage; and the process of its preparation comprising at least two repetitive steps of crystallization from one or more organic solvent by dissolving 2-methyl-4-(4-methyl-1-piperazinyl)-10H-thieno[2,3-b][1,5]benzodiazepine in said solvent and allowing crystallization to occur; wherein in at least one step the solution is purified by treating with a solid adsorbent material and filtering; and wherein in the last step the crystalline material is subjected to drying.

19 Claims, No Drawings

CRYSTALLINE FORM I OF 2-METHYL-4-(4-MENTHYL-1-PIPERAZINYL) 10H THIENO [2,3-B][1,5]BENZODIAZEPINE

FIELD OF THE INVENTION

This invention relates to crystalline Form I of 2-methyl-4-(4-methyl-1-piperazinyl)-10H-thieno[2,3-b][1,5] benzodiazepine, a compound of formula 1, having a stable colour at ambient conditions of storage and also to the process of its preparation. 2-methyl4-(4-methyl-1-piperazinyl)-10H-thieno[2,3-b][1,5]benzodiazepine, commonly known as olanzapine (INN Name) is used as an antipsychotic agent.

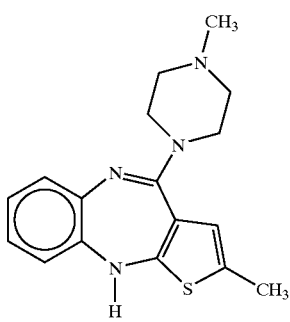

Formula 1

BACKGROUND OF THE INVENTION

U.S. Pat. No. 5,229,382 (hereinafter described as '382) discloses the preparation of 2-methyl-4-(4-methyl-1-piperazinyl)-10H-thieno[2,3-b][1,5]benzodiazepine, or an acid addition salt thereof by reacting N-methyl piperazine with 4-amino-2-methyl-10H-thieno[2,3-b][1,5] benzodiazepine hydrochloride. The anhydrous 2-methyl-4-(4-methyl-1-piperazinyl)-10H-thieno[2,3-b][1,5] benzodiazepine obtained by the process of this patent is referred to herein as Form I. Form I has been reported to be metastable and to change its colour on standing thus being unsuitable for commercial use in pharmaceutical formulation.

U.S. Pat. No. 5,736,541 (hereinafter described as '541) claims a novel crystal form (Form II) of olanzapine which is substantially pure, solvate free, anhydrous and pharmaceutically elegant. This novel crystal form is free from Form I and contamination by solvates such as water or acetonitrile and has satisfactory colour stability. The '541 patent provides olanzapine Form II having a typical x-ray powder diffraction pattern as represented by the d (interplanar spacing) values: 10.2689, 8.577, 7.4721, 7.125, 6.1459, 6.071, 5.4849, 5.2181, 5.1251, 4.9874, 4.7665, 4.7158, 4.4787, 4.3307, 4.2294, 4.141, 3.9873, 3.7206, 3.5645, 3.5366, 3.3828, 3.2516, 3.134, 3.0848, 3.0638, 3.0111, 2.8739, 2.8102, 2.7217, 2.6432, 2.6007.

Further, this patent designates the polymorph obtained by the process disclosed in '382 patent as Form I having a typical x-ray powder diffraction pattern as represented by the d (interplanar spacing) values : 9.9463, 8.5579, 8.2445, 6.8862, 6.3787, 6.2439, 5.5895, 5.3055, 4.9815, 4.8333, 4.7255, 4.6286, 4.533, 4.4624, 4.2915, 4.2346, 4.0855, 3.8254, 3.7489, 3.6983, 3.5817, 3.5064, 3.3392, 3.2806, 3.2138, 3.1118, 3.0507, 2.948, 2.8172, 2.7589, 2.6597, 2.6336, 2.5956.

The nomenclature referred to in this patent for crystalline forms of 2-methyl-4-(4-methyl-1-piperazinyl)-10H-thieno [2,3-b][1,5]benzodiazepine is adopted herein.

The process disclosed in the '541 patent consists of obtaining technical grade olanzapine (that is olanzapine containing less than about 5% undesired related substances and preferably less than 1% undesired related substances) by adding water to a methanolic reaction mixture and filtering the solids. The technical grade olanzapine obtained is crystallized from anhydrous ethyl acetate as substantially pure Form II that is free from the undesired crystal Form I or solvates such as water, alcohol, ethylacetate or acetonitrile.

U.S. Pat. No. 5,703,232 (hereinafter described as '232) relates to lower alcohol solvates of olanzapine and a process for using such lower alcohol solvates to prepare anhydrous olanzapine crystalline form having a typical x-ray diffraction pattern with d (interplanar spacing) values substantially as follows 10.2689, 8.577, 7.4721, 7.125, 6.1459, 6.071, 5.4849, 5.2181, 5.1251, 4.9874, 4.7665, 4.7158, 4.4787, 4.3307, 4.2294, 4.141, 3.0873, 3.7206, 3.5645, 3.5366, 3.3828, 3.2516, 3.134, 3.0848, 3.0638, 3.0111, 2.8739, 2.8102, 2.7217, 2.6432, 2.6007. The patent labels this crystalline form as Form I and reverses the nomenclature adopted in the '541 patent. As compared to the '541 process where a technical grade olanzapine is precipitated by addition of excess water to a methanolic reaction mixture, the '232 process involves addition of a $C_1$–$C_3$ alcohol and isolating an alkanol solvate by cooling. The anhydrous crystalline form of olanzapine is prepared by recrystallizing the alkanol solvate from an appropriate solvent. The patent does not disclose anhydrous olanzapine crystalline form having a typical x-ray powder diffraction pattern as represented by d (interplanar spacing) values 9.9446, 8.5272, 8.1949, 6.8637, 6.3510, 5.4653, 4.8278, 4.7121, 4.5295, 4.2239, 4.0788, 3.8230, 3.7525, 3.6909, 3.4995, 3.3393, 3.1051, 2.9451, 2.8182, 2.7589, 2.5925, 2.3369, 2.0251, 1.9183; infrared absorbance bands at approximately 1456, 1365, 905, 757, 662 & 604 $cm^{-1}$ and having a stable colour upon storage under ambient conditions or a process for its preparation using two or more repetitive crystallization steps.

The above patents do not disclose anhydrous olanzapine crystalline form I having a stable colour upon storage under ambient conditions or a process for its preparation using two or more repetitive crystallization steps.

WO 9812199 relates to the dihydrate of olanzapine. Dihydrates B, D and E are claimed as intermediates for preparing Form II. The dihydrates are dried for a period of about 27–30 hours to yield olanzapine Form II.

Prior art suggests that Form I olanzapine is pharmaceutically unsuitable because its colour changes upon storage and exposure to air. Methods like charcoal treatment to remove undesired colour from the Form I olanzapine prepared by '382 were not successful. Anhydrous olanzapine crystalline Form I having a stable colour upon storage at ambient conditions is hitherto unknown.

OBJECT OF THE INVENTION

An object of the present invention is to provide crystalline Form I of 2-methyl-4-(4-methyl-1-piperazinyl)-10H-thieno [2,3-b][1,5]benzodiazepine and the process for preparation of Form I having a stable colour at ambient conditions of storage.

A further object of the present invention is to provide crystalline Form I of 2-methyl-4-(4-methyl-1-piperazinyl)-10H-thieno[2,3-b][1,5]benzodiazepine which is free from the solvent of crystallization and has desirable characteristics such as stable colour and stable crystalline form making it suitable for pharmaceutical formulation.

SUMMARY OF THE INVENTION

According to the broadest aspect the present invention provides crystalline Form I of 2-methyl-4-(4-methyl-1-piperazinyl) -10H-thieno[2,3-b][1,5]benzodiazepine having stable colour upon storage at ambient conditions.

According to a further aspect the present invention provides crystalline Form I of 2-methyl-4-(4-methyl-1-piperazinyl)-10H-thieno[2,3-b][1,5]benzodiazepine characterised by x-ray powder diffraction peaks at approximately 9.94, 8.53, 8.19, 6.86, 6.35, 5.47, 4.83, 4.71, 4.53, 4.22, 4.08, 3.82, 3.75, 3.69, 3.50, 3.34, 3.11, 2.94, 2.82, 2.76, 2.59, 2.34, 2.03, 1.92d (interplanar spacing) values; infrared absorbance bands at approximately 1456, 1365, 905, 757, 662 & 604 cm$^{-1}$ and having stable colour upon storage at ambient conditions.

The present invention also provides a process for preparation of the crystalline Form I comprising at least two repetitive steps of crystallization from one or more organic solvent by dissolving 2-methyl-4-(4-methyl-1-piperazinyl)-10H-thieno[2,3-b][1,5]benzodiazepine in said organic solvent and allowing crystallization to occur; wherein in at least one step the solution is purified by treating with a solid adsorbent material and filtering; and wherein in the last step the crystalline material is subjected to drying.

DETAILED DESCRIPTION OF THE INVENTION

The crystalline Form I of 2-methyl-4-(4-methyl-1-piperazinyl)-10H-thieno[2,3-b][1,5]benzodiazepine of the present invention has a typical x-ray powder diffraction pattern as represented by d (interplanar spacing) values 9.9446, 8.5272, 8.1949, 6.8637, 6.3510, 5.4653, 4.8278, 4.7121, 4.5295, 4.2239, 4.0788, 3.8230, 3.7525, 3.6909, 3.4995, 3.3393, 3.1051, 2.9451, 2.8182, 2.7589, 2.5925, 2.3369, 2.0251, 1.9183; infrared absorbance bands at approximately 1456, 1365, 905, 757, 662 & 604 cm$^{-1}$ and a stable colour. The crystalline Form I of the present invention shows no change in colour, infrared spectrum and x-ray diffractogram at ambient conditions of storage such as about 15° C. to 35° C. and about 40% to 90% RH. The crystalline Form I of the present invention is stable even under accelerated conditions of storage, for example, no changes in colour, infra-red spectrum and x-ray diffractogram are observed upon storage at accelerated conditions for one month at 40° C. and 75% relative humidity or for 25 days at 75–80° C.

The crystalline Form I of the present invention is prepared by a process comprising at least two repetitive steps of crystallization from one or more organic solvent by dissolving 2-methyl-4-(4-methyl-1-piperazinyl)-10H-thieno[2,3-b][1,5]benzodiazepine in said organic solvent and allowing crystallization to occur; wherein in at least one step the solution is purified by treating with a solid adsorbent material and filtering; and wherein in the last step the crystalline material is subjected to drying.

According to one embodiment of the present invention the organic solvent is selected from the group consisting of aliphatic, cyclic or aromatic hydrocarbons, alkanols, esters, ketones, ethers, nitriles, amides, sulfoxides and the like.

In a preferred embodiment of the present invention solvent is an alkanol selected from $C_1$ to $C_4$ alkanol or its admixture with water. More preferably the alkanol is ethanol.

According to the present invention a solution of 2-methyl-4-(4-methyl-1-piperazinyl)-10H-thieno[2,3-b][1,5]benzodiazepine in the organic solvent is prepared by stirring or heating one gram of 2-methyl-4-(4-methyl-1-piperazinyl)-10H-thieno[2,3-b][1,5]benzodiazepine in 5 to 25 parts by volume of the solvent, more preferably 10 to 20 parts by volume, the most preferred being 15 parts by volume. The solution is allowed to stand for crystallization to occur. Preferably the solution is cooled to aid crystallization.

According to an embodiment of the present invention the dissolution of 2-methyl-4-(4-methyl-1-piperazinyl)-10H-thieno[2,3-b][1,5]benzodiazepine may be achieved by heating the organic solvent containing 2-methyl-4-(4-methyl-1-piperazinyl)-10H-thieno[2,3-b][1,5]benzodiazepine. Preferably the organic solvent is heated to a temperature greater than about 40° C., most preferably to reflux temperature.

In a particularly preferred embodiment of the present invention, the process comprises crystallization in two steps wherein in the first step the organic solvent used is a mixture of ethanol and water and in the second step the solvent is absolute ethanol. According to the present invention the mixture of ethanol and water used maybe in a ratio of 97:3 to 90:10 preferably 95:5 to 92:8 and the most preferred is 95:5 parts by volume. In this particular embodiment, the technical grade 2-methyl-4-(4-methyl-1-piperazinyl)-10H-thieno[2,3-b][1,5]benzodiazepine is dissolved in aqueous ethanol 90–97%, preferably 93–95% at a temperature of 40–80° C., preferably 77–78° C. to obtain a clear solution. The clear solution is treated with the solid adsorbent material at 40–80° C., preferably at reflux temperature, filtered and the filtrate cooled to 60–65° C., preferably 8–10° C. to obtain crystals of 2-methyl-4-(4-methyl-1-piperazinyl)-10H-thieno[2,3-b][1,5]benzodiazepine. In the second step, these crystals are dissolved in absolute ethanol at a temperature of 40–80° C., preferably 77–78° C. to obtain a clear solution. The solution is then cooled, either rapidly to induce sudden crystallization or by a gradual cooling process with or without seeding of Form I crystals, in order to induce crystallization. The crystals are filtered containing 10 to 30% solvent hereinafter referred to wet crystals which may be subjected to drying.

According to one embodiment of the present invention the solid adsorbent material may be selected from neutral or alkaline alumina, silica, fuller's earth, activated charcoal and the like, the most preferred being activated charcoal.

The last or final crystallization step of the process of the present invention may be carried out with or without the presence of seed crystals.

According to one embodiment of the present invention crystallization is allowed to occur by chilling or seeding or scratching the glass of the reaction vessel or cooling and other such common techniques, preferably cooling and/or seeding.

According to the preferred embodiment of the present invention crystallization is allowed to occur by cooling the solution of 2-methyl-4-(4-methyl-1-piperazinyl)-10H-thieno[2,3-b][1,5]benzodiazepine in an organic solvent which may be seeded with a crystal of Form I of 2-methyl-4-(4-methyl- 1-piperazinyl)-10H-thieno[2,3-b][1,5]benzodiazepine. The seeding with Form I crystals is done, prior to a stage, wherein the initial crystallization is just about to commence i.e. at a temperature of about 35–70° C., preferably about 55–70° C.

According to another embodiment of the present invention in the last or final crystallization step the solution may be cooled in an ice bath or under refrigeration or by adding liquid nitrogen to the solution. The solution may be preferably cooled to below room temperature, preferably to about 8–10° C. to allow crystallization to occur. The solution may be allowed to cool for a sufficient time for crystallization to occur, for example period of 15 minutes to 8 hours. More preferably the cooling operation is performed such that the reflux temperature is brought to about 55–60° C. during a period of 1 hour to 3 hours, followed by cooling to about 30–35° C. during a period of 1 hour to 3 hours and then finally to 8–10° C. during a period of 1 hour to 3 hours.

According to the present invention at the end of the first or any intermediate crystallization step, other than the final crystallization step, wet crystals of 2-methyl-4-(4-methyl-1-piperazinyl)-10H-thieno[2,3-b][1,5]benzodiazepine are obtained. These wet crystals upon isolation may contain 10–30% w/v of the solvent. The wet crystals may be used as such in the next or final crystallization step or they could be dried at a temperature below 50° C., under atmospheric conditions.

According to the present invention in the last or final crystallization step the product may be dried using different techniques of drying like fluid bed drying, tray drying and rotatory drying techniques with or without application of vacuum and/or under inert conditions. Dryers that have rotational means at reduced pressures are preferred.

Examples of rotatory drying techniques that may be suitable include rota-cone and horizontal rotary vacuum dryers.

According to an embodiment of the present invention in the last or final crystallization step the product is dried at a temperature of about 25 to 55° C., preferably about 30 to 50° C. the most preferred is about 45 to 50° C.

Another embodiment of the present invention also provides a pharmaceutical composition comprising crystalline Form I of 2-methyl-4-(4-methyl-1-piperazinyl)-10H-thieno[2,3-b][1,5]benzodiazepine and a pharmaceutically acceptable carrier.

Preferably, the present invention provides a pharmaceutical composition comprising crystalline Form I of 2-methyl-4-(4-methyl-1-piperazinyl)-10H-thieno[2,3-b][1,5]benzodiazepine for use in the treatment of psychotic disorders and a pharmaceutically acceptable carrier.

Such compositions may be prepared by admixing crystalline Form I of 2-methyl-4-(4-methyl-1-piperazinyl)-10H-thieno[2,3-b][1,5]benzodiazepine especially 2 to 20 mg thereof, and a pharmaceutically acceptable carrier. Usually the compositions are adapted for oral administration. However, they may be adapted for other modes of administration, for example parenteral administration, sublingual or transdermal administration.

The compositions may be in the form of tablets, capsules, powders, granules, lozenges, transdermal patches, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone, fillers, for example lactose, sugar, maize-starch, calcium phosphate, sorbitol orglycine, tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The compositions are preferably in a unit dosage form in an amount appropriate for the relevant daily dosage.

Suitable dosages including unit dosages of the crystalline Form I of 2-methyl-4-(4-methyl-1-piperazinyl)-10H-thieno[2,3-b][1,5]benzodiazepine comprise 2.5, 5, 7.5, 10, 15 or 20 mg of the crystalline Form I of 2-methyl-4-(4-methyl-1-piperazinyl)-10H-thieno[2,3-b][1,5]benzodiazepine.

In the treatment the medicaments may be administered from 1 to 6 times a day, but most preferably 1 or 2 times per day.

Particular dosages of crystalline Form I of 2-methyl-4-(4-methyl-1-piperazinyl)-10H-thieno[2,3-b][1,5]benzodiazepine are 2.5, 5, 7.5, 10, 15 and 20 mg/day. Suitable dosages including unit dosages of crystalline Form I of 2-methyl-4-(4-methyl-1-piperazinyl)-10H-thieno[2,3-b][1,5]benzodiazepine, include the known dosages for these compounds as described or referred to in reference text books or the above mentioned publications. Thus a typical daily dosage of crystalline Form I of 2-methyl-4-(4-methyl-1-piperazinyl)-10H-thieno[2,3-b][1,5]benzodiazepine is in the range of from 2 to 20 mg, for example 10 mg per day.

The solid oral compositions may be prepared by conventional methods of blending, filling or tabletting known to those skilled in this art. Repeated blending operations may be used to distribute the active agent throughout those compositions employing large quantities of fillers. Such operations are of course conventional in the art. The tablets may be coated according to methods well known in normal pharmaceutical practice.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, a preservative and buffering agent can be dissolved in the vehicle. To enhance the stability, the composition can be frozen after filling into the vial and the water removed under vacuum.

Compositions may contain from 0.1% to 99% by weight, preferably from 10–60% by weight, of the active material, depending upon the method of administration.

Composition may, if desired, be in the form of a pack accompanied by written or printed instructions for use.

The invention is further illustrated but not restricted by the description in the following examples.

EXAMPLES

Example 1

Preparation of Wet Crystals of 2-Methyl-4-(4-methyl-1-piperazinyl)-10H-thieno[2,3-b][1,5]benzodiazepine from Technical 2-Methyl-4-(4-methyl-1-piperazinyl)-10H-thieno[2,3-b][1,5]benzodiazepine:

Charge 1.8 L of aqueous alcohol (95%) into a 2 L three-necked round bottom flask at 30±2° C. Add 100 g of technical 2-methyl-4-(4-methyl-1-piperazinyl)-10H-thieno[2,3-b][1,5]benzodiazepine to the flask and start stirring. Gradually heat the contents of flask to 77–78° C. so as to obtain a clear solution. Stir the contents for 15 mins at 77–78° C. Add 2 g of charcoal at 77–78° C. and stir the contents of flask for 30 mins. Filter the contents of the flask at 77–78° C. on a hyflo bed through a buchner funnel. Collect the filtrate and charge into a clean and dry 2 L three-necked round bottom flask. Allow the contents of flask to cool to 28±2° C, then cool it further to 10° C. using ice water bath and stir for 30 mins at 8–10° C. Filter the solid product and wash the product cake with chilled aqueous alcohol (95%/o) and suck dry to obtain 85 g (yield: 85% w/w) of wet crystals of 2-methyl-4-(4-methyl-1-piperazinyl)-10H-thieno[2,3-b][1,5]benzodiazepine.

Example 2

Preparation of Form-I of 2-Methyl-4- (4-methyl-1-piperazinyl)-10H-thieno[2,3-b][1,5]benzodiazepine from Wet Crystal 2-Methyl-4-(4-methyl-1-piperazinyl)-10H-thieno[2,3-b][1,5]benzodiazepine:

Method-1

85 g of wet crystals of 2-methyl-4-(4-methyl-1-piperazinyl)-10H-thieno[2,3-b][1,5]benzodiazepine along with 1.275 L of absolute ethanol is charged into 2 L three-necked round bottom flask and stirred at 30 ±2° C. The contents of the flask are gradually heated to 77–78° C. to obtain a clear solution and then stirred for 15 mins at 77–78° C. The contents of the flask are allowed to cool to 55–57° C. The contents of the flask are further cooled to 30–34° C. and then to 10° C. Stir the contents for 30 mins at 8–10° C. Filter the solid product and wash the product cake with chilled absolute alcohol and suck dry. Dry the product under vacuum at 47–50° C. on a rotavapour until constant weight to obtain 56 g of Form I (yield 65.9%)

No change in colour, Infrared spectrum (KBr) and X-ray diffractogram was observed when the product was stored at ambient conditions of storage viz. room temperature for one month and at accelerated conditions of storage like (a) 40° C. and 75% relative humidity for one month and (b) 75–80° C. for 25 days.

Example 3

Method-2

50 g of wet crystals of 2-methyl-4-(4-methyl-1-piperazinyl)-10H-thieno[2,3-b][1,5]benzodiazepine along with 0.75 L of absolute ethanol is charged into 2 L three-necked round bottom flask and stirred at 30±2° C. The contents of the flask are gradually heated to 77–78° C. to obtain a clear solution and then stirred for 15 mins at 77–78° C. Remove the oil bath and gradually allow the flask to cool to 55–57° C. During the process of cooling to 55–57° C. seed the solution with 2-methyl-4-(4-methyl-1-piperazinyl)-10H-thieno[2,3-b][1,5]benzodiazepine Form I at an interval of every 5° C. until the seed remains undissolved. The contents of the flask are further cooled to 30–34° C. and then to 10° C. Stir the contents for 30 mins at 8–10° C. Filter the solid product and wash the product cake with chilled absolute alcohol and suck dry. Dry the product under vacuum at 47–50° C. on a rotavapour until constant weight to obtain 33 g (yield 66% w/w) of Form I.

Example 4

Method-3

20 g of wet crystals of 2-methyl-4-(4-methyl-1-piperazinyl)-10H-thieno[2,3-b][1,5]benzodiazepine along with 0.3 L of absolute ethanol is charged-into 2 L three-necked round bottom flask and stirred at 30±2° C. The contents of the flask are gradually heated to 77–78° C. to obtain a clear solution and then stirred for 15 mins at 77–78° C. Remove the oil bath and cool it rapidly by pouring 1.0 L of liquid nitrogen so as to rapidly cool it to 10° C. over a period of 5–10 minutes. Stir the contents of the flask for 15 mins at 8–10° C. Filter the solid product and wash the product cake with chilled absolute alcohol and suck dry. Dry the product under vacuum at 47–50° C. on a rotavapour until constant weight to obtain 14.12 g (yield 70.6% w/w) of Form I.

Example 5

50 g of wet crystals of 2-methyl-4-(4-methyl-1-piperazinyl)-10H-thieno[2,3-b][1,5]benzodiazepine is dried at 45–50° C. to obtain crude of 2-methyl-4-(4-methyl-1-piperazinyl)-10H-thieno[2,3-b[]1,5]benzodiazepine.

Example 6

The crystal form of 2-methyl-4-(4-methyl-1-piperazinyl)-10H-thieno[2,3-b][1,5]benzodiazepine prepared as per Examples 1, 2 and 3 was subjected to powder x-ray diffraction analysis using copper x-ray source at 1.541λ.

We claim:

1. Crystalline Form I of 2-methyl-4-(4-methyl-1-piperazinyl)-10H-thieno[2,3-b][1,5]benzodiazepine characterized by x-ray powder diffraction peaks at approximately 9.94, 8.53, 8.19, 6.86, 6.35, 5.47, 4.83, 4.71, 4.53, 4.22, 4.08, 3.82, 3.75, 3.69, 3.50, 3.34, 3.11, 2.94, 2.82, 2.76, 2.59, 2.34, 2.03, 1.92 d (interplanar spacing) values and having stable colour upon storage at ambient conditions.

2. A process for preparing crystalline Form I of 2-methyl-4-(4-methyl-1-piperazinyl)-10H-thieno[2,3-b][1,5]benzodiazepine comprising
at least two repetitive steps of crystallization wherein said 2-methyl-4-(4-methyl-1-piperazinyl)-10H-thieno[2,3-b][1,5]benzodiazepine is dissolved in one or more organic solvent and crystallization is allowed to occur;
wherein at least one step of crystallization comprises purification of the solution by treating the same with a solid adsorbent material and filtering; and wherein the last step of crystallization comprises subjecting the crystalline material to drying.

3. A process for preparing the crystalline Form I according to claim 2 wherein the organic solvent is selected from a $C_1$ to $C_4$ alkanol; optionally admix with water wherein the $C_1$ to $C_4$ alkanol to water ratio is 95 to 5 parts by volume.

4. A process for preparing the crystalline Form I according to claim 3 wherein the $C_1$ to $C_4$ alkanol is ethanol.

5. A process for preparing the crystalline Form I according to claim 2 wherein the dissolution is carried out by heating to a temperature greater than about 40° C.

6. A process for preparing the crystalline Form I according to claim 5 wherein it is heated to reflux temperature.

7. A process for preparing the crystalline Form I according to claim 2 wherein crystallization is allowed to occur by cooling and/or seeding.

8. A process for preparing the crystalline Form I according to claim 7 wherein seed crystals of Form I of 2-methyl-4-(4-methyl-1-piperazinyl)-10H-thieno[2,3-b][1,5]benzodiazepine are added during cooling.

9. A process for preparing the crystalline Form I according to claim 8 wherein seed crystals are added during cooling to a temperature of about 35–70° C.

10. A process for preparing the crystalline Form I according to claim 9 wherein seed crystals are added during cooling to a temperature of about 55–70° C.

11. A process for preparing the crystalline Form I according to claim 7 wherein the solution is cooled to about 8–10° C.

12. A process for preparing the crystalline Form I according to claim 2 wherein the solid adsorbent material is selected from alumina, silica, fuller's earth and activated charcoal.

13. A process for preparing the crystalline Form I according to claim 2 wherein the process comprises two recrystallization steps wherein in the first step the organic solvent used is a mixture of ethanol and water and in the second step the solvent used is absolute ethanol.

14. A process for preparing the crystalline Form I according to claim 2 wherein drying is carried out at 25–55° C. with or without vacuum and/or under inert conditions.

15. A process for preparing the crystalline Form I according to claim 14 wherein drying is carried out in a rotary vacuum dryer at about 45–50° C.

16. Crystalline Form I of 2-methyl-4-(4-methyl-1-piperazinyl)-10H-thieno[2,3-b][1,5]benzodiazepine characterized by x-ray powder diffraction peaks at approximately 9.94, 8.53, 8.19, 6.86, 6.35, 5.47, 4.83, 4.71, 4.53, 4.22, 4.08, 3.82, 3.75, 3.69, 3.50, 3.34, 3.11, 2.94, 2.82, 2.76, 2.59, 2.34, 2.03, 1.92 d (interplanar spacing) values and having stable colour upon storage at ambient conditions when produced by the process according to claim 2.

17. Crystalline Form I of 2-methyl-4-(4-methyl-1-piperazinyl)-10H-thieno[2,3-b][1,5]benzodiazepine characterized by infrared absorbance bands at approximately 1456, 1365, 905, 757, 662 and 604 $cm^{-1}$ and having stable colour upon storage at ambient conditions when produced by the process according to claim 2.

18. A pharmaceutical composition comprising crystalline Form I of 2-methyl-4-(4-methyl-1-piperazinyl)-10H-thieno[2,3-b][1,5]benzodiazepine according to claim 1 and a pharmaceutically acceptable carrier, wherein said pharmaceutical composition is a solid and has a stable colour upon storage at ambient conditions.

19. A method of treatment of psychotic disorders comprising administering therapeutic doses of pharmaceutical composition according to claim 18.

* * * * *